United States Patent
Gallis et al.

(10) Patent No.: US 9,186,307 B2
(45) Date of Patent: Nov. 17, 2015

(54) TREATED SILICAS AND METAL SILICATES FOR IMPROVED CLEANING IN DENTIFRICE

(71) Applicant: JM Huber Corporation, Atlanta, GA (US)

(72) Inventors: Karl W. Gallis, Perryville, MD (US); William J. Hagar, Perryville, MD (US); Patrick McGill, Darlington, MD (US); Terry W. Nassivera, North East, MD (US)

(73) Assignee: J.M. Huber Corporation, Atlanta, GA (US)

( * ) Notice: Subject to any disclaimer, the term of this patent is extended or adjusted under 35 U.S.C. 154(b) by 148 days.

(21) Appl. No.: 13/835,819

(22) Filed: Mar. 15, 2013

(65) Prior Publication Data

US 2014/0140938 A1      May 22, 2014

Related U.S. Application Data

(60) Provisional application No. 61/727,831, filed on Nov. 19, 2012.

(51) Int. Cl.

| | | |
|---|---|---|
| *A61Q 11/00* | (2006.01) | |
| *A61K 8/25* | (2006.01) | |
| *A61K 8/26* | (2006.01) | |
| *A61K 6/00* | (2006.01) | |
| *A61K 8/19* | (2006.01) | |
| *A01N 59/06* | (2006.01) | |
| *C01B 33/193* | (2006.01) | |
| *A61K 8/02* | (2006.01) | |

(52) U.S. Cl.
CPC . *A61K 8/25* (2013.01); *A01N 59/06* (2013.01); *A61K 6/007* (2013.01); *A61K 8/0241* (2013.01); *A61K 8/19* (2013.01); *A61K 8/26* (2013.01); *A61Q 11/00* (2013.01); *C01B 33/193* (2013.01); *A61K 2800/61* (2013.01)

(58) Field of Classification Search
CPC ............. A61K 8/25; A61K 8/19; A61K 8/26; A61K 6/007; A61Q 11/00; A01N 59/06
USPC ............................................ 424/49, 684, 724
See application file for complete search history.

(56) References Cited

U.S. PATENT DOCUMENTS

| | | | |
|---|---|---|---|
| 2,739,073 A | 3/1956 | Leonard | |
| 2,848,346 A | 8/1958 | Leonard | |
| 4,340,583 A | 7/1982 | Wason | |
| 4,420,321 A | 12/1983 | Wilson | |
| 4,421,527 A | 12/1983 | Wason | |
| 5,891,421 A | 4/1999 | McGill et al. | |
| 6,616,916 B1 | 9/2003 | Karpe et al. | |
| 2011/0206746 A1 * | 8/2011 | Hagar et al. | 424/401 |
| 2011/0206749 A1 * | 8/2011 | Gallis et al. | 424/401 |
| 2012/0039782 A1 * | 2/2012 | Nicholas | 423/263 |
| 2014/0127145 A1 | 5/2014 | Deckner et al. | |

FOREIGN PATENT DOCUMENTS

| | | |
|---|---|---|
| WO | WO 93/23007 | 11/1993 |
| WO | WO 9323007 A1 * | 11/1993 |
| WO | WO 2011/103226 | 8/2011 |
| WO | WO 2011/150004 | 12/2011 |
| WO | WO 2014/071284 | 5/2014 |

OTHER PUBLICATIONS

International Search Report for Application No. PCT/US2013/067087 dated Aug. 5, 2014, 4 pages.

* cited by examiner

*Primary Examiner* — Frederick Krass
*Assistant Examiner* — Tracy Liu
(74) *Attorney, Agent, or Firm* — Merchant & Gould P.C.

(57) ABSTRACT

Treated silica materials are disclosed, together with methods of making such materials and dentifrice compositions comprising the treated silica materials.

24 Claims, No Drawings

TREATED SILICAS AND METAL SILICATES FOR IMPROVED CLEANING IN DENTIFRICE

CROSS REFERENCE TO RELATED APPLICATIONS

The present application claims the benefit of priority to U.S. Provisional Patent Application Ser. No. 61/727,831, filed on Nov. 19, 2012, which is hereby incorporated by reference in its entirety.

BACKGROUND

1. Technical Field

The present disclosure relates to silica and silicate materials, and specifically to treated silica and metal silicate materials that can provide improved cleaning properties in a dentifrice composition.

2. Technical Background

Conventional dentifrice compositions comprise an abrasive substance to assist in the removal of dental deposits. One such dental deposit is pellicle, a protein film which adheres strongly to tooth surfaces and often contains brown or yellow materials that can result in tooth discoloration. A dentifrice should be sufficiently abrasive to clean the tooth surface, but not so abrasive as to damage the hard tissues of the tooth.

The performance of the dentifrice can thus be highly sensitive to the aggressiveness of the abrasive substance. Synthetic low-structure silica materials have been utilized as abrasive substances due to their effectiveness as abrasives, as well as their low toxicity characteristics and compatibility with other dentifrice components, such as sodium fluoride.

To date, conventional abrasive materials have limitations associated with maximizing cleaning and minimizing dentin abrasion, as well as complexity in terms of manufacturing procedures. Accordingly, there exists a general need to develop new dental abrasives and dentifrices thereof that exhibit high pellicle film cleaning properties and have acceptable dentin abrasion levels. This need and other needs are satisfied by the compositions and methods of the present disclosure.

SUMMARY

In accordance with the purpose(s) of the invention, as embodied and broadly described herein, this disclosure, in one aspect, relates to silica and silicate materials, and specifically to treated silica and metal silicate materials that can provide improved cleaning properties in a dentifrice.

In one aspect, the present disclosure provides a method for preparing a silica material, the method comprising: heat treating a silica material comprising a metal compound, wherein the metal has a Mohs hardness value of at least about 5.5 in its oxide form, and wherein heat treating comprises heating the silica material at a temperature and for a period of time sufficient to dehydrate at least a portion of the metal compound disposed on a surface of the material.

In one aspect, the present disclosure provides a method for preparing a dentifrice composition, the method comprising: heat treating a silica material at a temperature of from about 400° C. to about 900° C. to form a heat treated silica material, and then contacting the heat treated silica material with one or more dentifrice components to form a dentifrice composition.

In another aspect, the present disclosure provides a silica material having one or more of the following: a metal ion disposed on a surface thereof at a concentration of up to about 10 wt. %; a loss on ignition at 900° C. of less than about 3 wt. %; or an increased degree of polymerization as compared to a conventional silica material not exposed to a heat treatment step.

In another aspect, the present disclosure provides a silica material having an increased Einlehner abrasion value of at least about 150%, as compared to a conventional non heat treated precipitated silica and having an increase in RDA value still within the acceptable RDA range after heat treatment, as compared to a conventional non heat treated precipitated silica.

In yet another aspect, the present disclosure provides a dentifrice composition comprising the silica material of any of the preceding claims Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, example methods and materials are now described.

As used herein, unless specifically stated to the contrary, the singular forms "a," "an" and "the" include plural referents unless the context clearly dictates otherwise. Thus, for example, reference to "a filler" or "a solvent" includes mixtures of two or more fillers, or solvents, respectively.

As used herein, the terms "optional" or "optionally" means that the subsequently described event or circumstance can or can not occur, and that the description includes instances where said event or circumstance occurs and instances where it does not.

For purposes of this invention, a "dentifrice" has the meaning defined in Oral Hygiene Products and Practice, Morton Pader, Consumer Science and Technology Series, Vol. 6, Marcel Dekker, N.Y. 1988, p. 200, which is incorporated herein by reference. Namely, a "dentifrice" is "... a substance used with a toothbrush to clean the accessible surfaces of the teeth. Dentifrices are primarily composed of water, detergent, humectant, binder, flavoring agents, and a finely powdered abrasive as the principal ingredient . . . a dentifrice is considered to be an abrasive-containing dosage form for delivering anti-caries agents to the teeth." Dentifrice formulations contain ingredients which must be dissolved prior to incorporation into the dentifrice formulation (e.g. anti-caries agents such as sodium fluoride, sodium phosphates, flavoring agents such as saccharin).

The Brass Einlehner (BE) Abrasion test used to measure the hardness of the precipitated silicas/silica gels reported in this application is described in detail in U.S. Pat. No. 6,616,916, incorporated herein by reference, involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams brass lost from the Fourdrinier wire screen per 100,000 revolutions. The result, measured in units of mg loss, can be characterized as the 10% brass Einlehner (BE) abrasion value.

The Radioactive Dentin Abrasion (RDA) values of dentifrices containing the silica compositions used in this invention are determined according to the method set forth by Hefferen, Journal of Dental Res., July-August 1976, 55 (4), pp. 563-573, and described in Wason U.S. Pat. Nos. 4,340,583, 4,420,312 and 4,421,527, which publications and patents are incorporated herein by reference.

The cleaning property of dentifrice compositions is typically expressed in terms of Pellicle Cleaning Ratio ("PCR") value. The PCR test measures the ability of a dentifrice composition to remove pellicle film from a tooth under fixed brushing conditions. The PCR test is described in "In Vitro Removal of Stain with Dentifrice" G. K. Stookey, et al., J. Dental Res., 61, 1236-9, 1982. Both PCR and RDA results vary depending upon the nature and concentration of the components of the dentifrice composition. PCR and RDA values are unitless.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

As briefly described above, the present disclosure provides silica and silicate materials that can be used in dentifrice compositions, methods for the preparation thereof, and dentifrice compositions comprising the inventive silica and silicate materials.

In the oral care industry, it would be desirable to have dentifrice materials with improved cleaning properties. It would also be advantageous for such dentifrice materials to exhibit moderate dentin and enamel abrasion properties, so as to not damage teeth during repeated use. Zinc and phosphate salts have been added to dentifrice materials and can result in small improvements in pellicle cleaning ratios (PCR), but further improvements are needed. Manufacturers have traditionally used high hardness abrasive materials, such as $\alpha$-alumina (i.e., corundum), but these materials can be expected to exhibit higher levels of enamel abrasion (REA) and a lack of fluoride availability.

In one aspect, the silica materials of the present disclosure can provide improved cleaning (e.g., PCR), while maintaining desirable RDA and/or REA values. In a further aspect, the silica materials can also provide desirable fluoride availability. In various aspects, the silica materials of the present disclosure comprise heat treated silica materials. In another aspect, the silica materials of the present disclosure comprise one or more metal ions present in their oxide form.

In one aspect, precipitated silica materials can be produced by the destabilization and precipitation of amorphous silica from soluble alkaline silicates by the addition of a mineral acid, acid gas, or acidulating agent under conditions in which primary particles initially formed tend to associate with each other, but without agglomeration into a three-dimensional gel structure.

Silica

Silica materials suitable for use in dentifrice compositions can comprise synthetically produced, precipitated silicas. In one aspect, the silica material can be a low-structure silica material. These silica materials can be produced using various procedures. In one aspect, a silicate compound, such as, for example, sodium silicate, can be contacted with a mineral acid to form a silicate solution. The silicate solution can then be combined with sulfuric acid and amorphous silica particles can be precipitated.

The silicate compound can comprise any silicate compound suitable for use in preparing a precipitated silica material. In various aspects, any suitable alkali metal silicate can be used with the methods described herein, including metal silicates, disilicates, and the like. In one aspect a water soluble silicate, such as, for example, a potassium silicate, a sodium silicate, or a combination thereof, can be used. In other aspects, a silicate compound having a desirable metal:silicate molar ratio (MR) can be selected. For example, sodium silicates can generally have a metal:silicate molar ratio of from about 1:1 to about 1:3.5. In one aspect, the silicate compound can have a molar ratio of from about 1:1 to about 1:3.5, for example, about 1:1, 1:1.25, 1:1.5, 1:1.75, 1:2, 1:2.25; 1:2.5; 1:2.75; 1:3, 1:3.25, or 1:3.5; or from about 1:2.5 to about 1:3.5, for example, about 1:2.5; 1:2.75; 1:3, 1:3.25, or 1:3.5. In another aspect, the silicate compound can have a molar ratio of about 1:3.32.

In one aspect, the silicate compound, such as, for example, sodium silicate, can be contacted with a mineral acid to produce a silicate solution. In general, any mineral acid capable of at least partially dissolving the silicate compound and forming a silicate solution can be used. In another aspect, the selection of a particular mineral acid can vary, depending upon the specific silicate compound being used. In various aspects, the mineral acid can comprise nitric acid, hydrochloric acid, phosphoric acid, boric acid, hydrofluoric acid, or a combination thereof. In other aspects, other suitable acids can be utilized in addition to or in lieu of any acid specifically recited herein. The silicate compound and acid can be contacted in any suitable ratio so as to provide a solution having a desirable silicate concentration. In one aspect, the solution comprises from about 8 wt. % to about 35 wt. % silicate, for example, about 8, 9, 11, 13, 15, 17, 19, 21, 23, 25, 27, 29, 31, 33, or 35 wt. % silicate. In another aspect, the solution comprises from about 8 wt. % to about 20 wt. % silicate, for example, about 8, 10, 12, 14, 16, 18, or 20 wt. % silicate. In a specific aspect, the silicate solution can comprise about 19.5 wt. % silicate. In other aspects, the resulting silicate solution can have a silicate concentration less than or greater than any value specifically recited herein, and the present disclosure is intended to cover such solutions. In still other aspects, silicate solutions are commercially available and can be purchased and utilized as-is (e.g., from Sigma-Alrich Corporation, St. Louis, Mo., USA).

In another aspect, the silicate solution can have a silicate concentration of from about 2 wt. % to about 10 wt. %, for example, about 2, 2.5, 3, 3.5, 4, 4.5, 5, 5.5, 6, 6.5, 7, 7.5, 8, 8.5, 9, 9.5, or 10 wt. %. In yet another aspect a silicate solution having a higher concentration, for example, about 20 wt. %, can be diluted in water to a lower concentration as described herein. For example, a quantity of a 19.5 wt. % silicate solution can be diluted to a concentration of about 5.5 wt. %.

The silicate solution can optionally be heated, for example, to about 75° C., about 80° C., about 85° C., about 87° C., about 90° C., or higher, and/or stirred.

Dopant Metal

In one aspect, the resulting precipitated silica material comprises one or more metal ions. In another aspect, the metal ions, if present, have a Mohs hardness value of at least about 5.5 in their oxide form. In various aspects, the metal ions can comprise aluminum, tin, or a combination thereof. In other aspects, other metal ions not specifically recited herein can be used, and the present disclosure is not intended to be limited to the metal ions recited herein. In a specific aspect, the metal ion comprises aluminum.

A metal ion, if present, can be introduced using a salt, for example, a soluble salt of the metal. In one aspect, such a metal salt can be at least partially solvated in an aqueous solution, a sulfuric acid solution, or a silicate solution. In one aspect, the metal salt can comprise a sulfate, a nitrate, a phosphate, a carbonate, or a combination thereof. In another aspect, the metal salt can comprise a sulfate, a nitrate, or a combination thereof. In various exemplary aspects, the metal salt can comprise aluminum sulfate, stannous nitrate, or a combination thereof.

The silicate solution, metal salt, and an acidulating agent, such as, for example, sulfuric acid, can then be contacted. The concentration and/or pH of the acidulating agent can be any concentration and/or pH suitable for use in preparing a precipitated silica material. In various aspects, the acidulating agent can comprise from about 5 wt. % to about 35 wt. % sulfuric acid, for example, about 5, 7, 9, 11, 13, 15, 17, 19, 21, 23, 25, 27, 29, 31, 33, or 35 wt. %; or from about 12 wt. % to about 22 wt. % sulfuric acid, for example, about 12, 13, 14, 15, 16, or 17 wt. % sulfuric acid.

In one aspect, one or more metal salts can be dissolved in the acidulating agent prior to contacting with the silicate. In another aspect, the metal salt, if present, can be dissolved in water or an acidic solution to be subsequently contacted with the acidulating agent and/or silicate solution. The concentration of the metal salt can vary, depending upon the reaction conditions and concentration of other reactants, and the present invention is not intended to be limited to any particular metal salt concentration. In one aspect, the metal salt concentration can be from about 0.2 N to about 0.4 N, for example, about 0.2, 0.22. 0.24, 0.26, 0.28, 0.29, 0.3, 0.32, 0.34, 0.36, 0.38, or 0.4 N. In another aspect, a sulfuric acid solution comprising, for example, aluminum sulfate, can have an aluminum concentration of from about 0.10 mol/L to about 0.20 mol/L, for example, about 0.10, 0.11, 0.12, 0.13, 0.14, 0.15, 0.16, 0.17, 0.18, 0.19, or 0.20 mol/L. Similarly, a sulfuric acid solution comprising, for example, stannous nitrate, can have a tin concentration of from about 0.25 mol/L to about 0.35 mol/L, for example, about 0.25, 0.26, 0.27, 0.28, 0.29, 0.30, 0.31, 0.32, 0.33, 0.34, or 0.35 mol/L.

In a specific aspect, a quantity of diluted, for example, about 5.5 wt. %, silicate solution can be disposed in a vessel, and then additional silicate solution and a solution of sulfuric acid containing a dissolved metal salt can simultaneously or substantially simultaneously be added to the vessel. In such an aspect, the solution in the vessel can optionally be heated and/or stirred during reaction.

The silicate solution and acidulating agent, for example, comprising the dissolved metal salt, can be added to the vessel over a period of time. In one aspect, the silicate solution, acidulating agent, metal salt, or any combination thereof, can be added slowly so as to allow at least partial mixing in the reaction vessel. In another aspect, the silicate solution and the acidulating agent can be added simultaneously or substantially simultaneously. In various aspects, the addition ratio of silicate solution to acidulating agent, for example, comprising a metal salt, if present, can be about from about 1:0.1 to about 1:0.6, for example, about 1:0.1, 1:0.15, 1:0.2, 1:0.25, 1:0.3, 1:0.33, 1:0.35, 1:0.4, 1:0.45, 1:0.5, 1:0.55, 1:0.6. In another aspect, the addition ratio of silicate solution to acidulating agent can be about 1:0.33, such that, for example, the silicate solution is added at a rate of about 1.1 L/min and optionally a metal salt containing sulfuric acid solution is simultaneously added at a rate of about 0.33 L/min.

The silicate solution and acidulating agent can be added for a fixed period of time or until exhausted. In one aspect, addition of the silicate solution can be stopped after a period of time, wherein addition of the acidulating agent continues for an additional period of time. In one aspect, the addition of the acidulating agent can be continued until a desired pH is reached in the reaction vessel. In such an aspect, the acidulating agent can be added until the pH in the reaction vessel is from about 4.5 to about 6.5, for example, about 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, or 6.5; or from about 5.3 to about 5.7, for example, about 5.3, 5.4, 5.5, 5.6, or 5.7.

In another aspect, addition of the silicate solution and/or acidulating agent can be stopped at any desired time and the pH of the reaction vessel subsequently adjusted to a desired value.

In another aspect, the silicate solution can be neutralized or at least partially neutralized by contacting with a metal salt or a solution thereof, without the need for an acid.

After contacting the silicate solution, the acidulating agent, and the metal salt, the resulting solution can be allowed to digest for a period of time. In one aspect, the solution can be allowed to digest at a temperature of about 90° C. for a period of at least about 10 minutes. In other aspects, a digestion step, if performed, can be performed for any suitable length of time and at any suitable temperature, and one of skill in the art, in possession of this disclosure, could readily determine appropriate digestion conditions. After digestion, the resulting precipitated silica material can be separated, for example, by filtration, from the solution. The separated silica material can optionally be washed to remove all or a portion of the acid and any unreacted, dissolved silicate or metal salt. In one aspect, the separated silica material can be washed, for example, with deionized water, until a conductivity of about 1,500 μS is reached. In other aspects, the separated silica material can be utilized as-is, or can be washed to a greater or lesser extent that that specifically described herein. In another aspect, the precipitated silica material can be dried, for example, by placing in a 105° C. oven overnight. In another aspect, the precipitated silica material can be spray dried.

If desired, the precipitated silica material can optionally be processed to achieve a desired average particle size or particle size distribution. In various aspects, the precipitated silica can be milled and/or ground to a desired average particle size, for example, of about 10 μm.

In one aspect, the reaction (e.g., contacting) of the silicate solution, acidulating agent, and metal salt can be conducted at an elevated temperature and/or while stirring so as to avoid the formation of a gel or aggregation of silica particles. In other aspects, it should be understood that the method of contacting and/or mixing, concentration and addition rates of reactants, temperature, and pH can each affect the properties of the resulting precipitated silica.

In one aspect, the preparation of a precipitated silica can be conducted as described in one or more of U.S. Pat. Nos. 2,739,073, 2,848,346, and 5,891,421, which are hereby incorporated by reference in their entirety for the purpose of disclosing methods for preparing precipitated silica materials. In other aspects, one of skill in the art, in possession of this disclosure, could readily determine appropriate reactants and reaction conditions to prepare a desired precipitate silica. In another aspect, the process to prepare a precipitated silica containing a metal ion as described herein can be performed in a batch process, a semi-continuous process, or a continuous process. In one aspect, all or a portion of the steps are performed in a batch process. In another aspect, the process can be at least partially continuous, wherein a silicate solution and an acidulating agent comprising a dissolved metal salt can be continuously fed into a loop reaction zone, wherein at least a portion of the acidulating agent, metal salt, and silicate react to form a precipitated silica.

Heat Treatment

In one aspect, the precipitated silica material prepared as described above likely comprises one or more hydrated metal species. As these species are typically soft, a heating step can be used to dehydrate the metal centers on the silica surface and produce, for example, metal oxides. In another aspect, the precipitated silica material can be prepared without the use of a metal salt having a desirable Mohs hardness. Any of a silica material prepared with a metal salt having a desirable Mohs hardness, a silica material prepared without such a metal salt, or a combination thereof, can be subjected to a heat treatment step as described herein.

The specific time and temperature at which a precipitated silica can be heated can vary. In one aspect, the precipitated silica can be heated for a time and at a temperature sufficient to increase the degree of polymerization in the Si framework of the material. In another aspect, the precipitated silica can be heated for a time and at a temperature sufficient to dehydrate metals that can be present on the surface of the silica material. In another aspect, the precipitated silica can be heated for a time and at a temperature sufficient to dehydrate at least a portion of metal ions present on the silica surface. In yet another aspect, the precipitated silica can be heated at a temperature less than that needed to induce significant phase transitions or morphology changes to the material. In still other aspects, the precipitated silica can be heated such that meso and macro porosity of the silica material are not significantly altered by the heat treatment.

In one aspect, the precipitated silica can be heated at a temperature of from about 400° C. to about 900° C., for example, about 400, 450, 500, 550, 600, 650, 700, 750, 800, 850, or 900° C. In another aspect, the precipitated silica can be heated at a temperature of from about 450° C. to about 650° C., for example about 450, 500, 550, 600, or 650° C. It should be appreciated that the time needed to dehydrate all or a portion of the metal species, if present on a silica surface, can vary depending on the temperature at which the material is heated. In one aspect, a precipitated silica can be heated at a temperature of about 550° C. for a period of greater than about 8 hours.

Heat Treated Silica Material

After heat treatment, the resulting silica material can optionally have a metal concentration (i.e., of the metal from the one or more metal salts) of up to about 10 wt. %, for example, about 0.5, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, or 10 wt. %. In another aspect, the resulting silica material can have a metal concentration of up to about 5 wt. %, for example, In yet other aspects, the resulting silica material can have a metal concentration of from about 1 wt. % to about 4 wt. %, for example, about 1, 1.25, 1.5, 1.75, 2, 2.25, 2.5, 2.75, 3, 3.25, 3.5, 3.75, or 4 wt. %.

In another aspect, the resulting silica material can have aluminum oxide present on the surface thereof, for example, at a concentration of from about 1 wt. % to about 4 wt. %. In yet another aspect, the resulting silica material can be absent of or substantially absent of a metal oxide, for example, when a metal salt dopant is not utilized.

In another aspect, the resulting silica material can exhibit a loss on ignition at 900° C. of less than about 3 wt. %, for example, about 1, 1.5, 2, 2.5, or 3 wt. %. In another aspect, the resulting silica material can exhibit a log on ignition at 900° C. of less than about 4 wt. %. In one aspect, conventional precipitated silica materials typically have loss on ignition values at 900° C. of between 4 and 6, whereas silica materials prepared as described herein, including heat treatment, can have a loss on ignition at 900° C. of about 2.5 or less.

In yet another aspect, the increased degree of polymerization as compared to a conventional precipitated silica can be detected via analytical techniques, such as, for example, solid state $^{29}$Si Nuclear Magnetic Resonance (NMR) spectroscopy.

Solid State NMR can be a powerful technique for determining the coordination environments of, for example, silicon atoms and the degree of polymerization of, for example, a siliceous solid. In solid state $^{29}$Si NMR, silicon species can be identified as M, $D^l$, $T^m$, and $Q^n$ (mono, di, tri and quaternary), denoting the degree of oxygen substitution on the central silicon atom, wherein the superscripts l, m and n refer to the number of (—O—Si) linkages. Therefore, $Q^n=Si(OSi)_n(OR)_{4-n}$ (n=1-4), $T^m=RSi(OSi)_m(OR)_{3-m}$ (m=1-3), $D^l=R_2Si(OSi)_l(OR)_{2-l}$ (l=1-2) and $M=R_3Si(OSi)$, where R is some other group, such as, for example, an organic group or hydrogen atom. As it pertains to inorganic siliceous materials disclosed herein, the quaternary species would be of greatest interest. Accordingly, a reduction in the silanol containing $Q^2$ and $Q^3$ species with a corresponding increase in the fully polymerized $Q^4$ species can be expected upon heat treatment as described herein.

In another aspect, enhanced resolution of the resulting spectra can be obtained by employing "magic angle spinning" (MAS) where the sample of interest is put into a rotor and spun at high speeds, for example, >3000 rpm, while being tilted at the "magic angle" of 54.74° with respect to the applied magnetic field. In such an aspect, this angle can be utilized because most of the interactions that cause broadening (dipolar interactions, chemical shift anisotropy (CSA) and differences in crystallite orientations) have an angular dependence of $3\cos^2\theta-1$, wherein $\theta$ is the angle between the applied magnetic field and the principal axis. In such an aspect, if $\theta=57.74°$, $3\cos^2\theta-1=0$ and the broadening effects are minimized. In addition, spinning at high rpm effectively can allow for averaging of the species since these solid materials are held in a fixed orientation. Therefore, $^{29}$Si MAS-NMR in essence can produce relatively detailed information on the composition of siliceous materials and any changes that can occur under various conditions.

In one aspect, the pellicle cleaning ratio of the inventive silica material and/or a dentifrice comprising the inventive silica material can be higher than a comparable precipitated silica not subjected to a heat treatment step and/or not having a metal oxide on the surface thereof. In another aspect, the pellicle cleaning ratio can be improved by at least about 10%, for example, about 10, 12, 14, 16, 18, 20, 25%, or more using the preparation methods described herein. In other aspects, the pellicle cleaning ration of the resulting silica material can range from about 90 to about 110, for example, about 90, 92, 94, 96, 98, 100, 102, 104, 106, 108, or 110. In other aspects, the pellicle cleaning ratio of the resulting silica material can be higher than 110, and the present invention is not intended to be limited to any particular pellicle cleaning ratio.

After heat treatment, the Einlehner abrasion values of the resulting silica material are significantly increased. In various aspects, the Einlehner abrasion values increase from about 90% to about 450%, for example, about 90, 100, 110, 120, 130, 140, 150, 175, 200, 225, 250, 250, 275, 300, 325, 350, 375, 400, 425, or 250%; or from about 120% to about 200%, for example, about 120, 125, 130, 125, 140, 145, 150, 160, 170, 180, 190, or 200% after heat treatment. In another aspect, the Einlehner abrasion value increases about 150% after heat treatment. In conventional precipitates silica materials, changes in the Einlehner abrasion values typically correspond to changes in RDA and/or REA values. Such a large increase in dentin abrasion would be unacceptable for use in dentifrice materials as continued use would result in damage to the tooth tissues. Surprisingly, the inventive precipitated silica materials exhibit significant increases in Einlehner abrasion values, as described above, without corresponding changes in RDA and/or REA values. In one aspect, Einlehner abrasion can be significantly increased while maintaining a desirable RDA and/or REA value. In another aspect, the RDA value of the resulting silica material can remain substantially the same or exhibit a small, acceptable increase after heat treatment. In one aspect, the RDA value after heat treatment remains within about 5% of the original value (prior to heat treatment). In another aspect, the RDA value can increase by up to about 25%, for example, about 5, 8, 12, 15, 18, 21, or 25% after heat treatment. In yet another aspect, the increase in RDA can be about 10% of the corresponding increase in Einlehner abrasion after heat treatment. For example, a heat treated precipitated silica, prepared using aluminum sulfate, can exhibit an increase in Einlehner abrasion after heat treatment of about 215%, whereas the corresponding RDA value increases by only about 22% after heat treatment. Thus, in one aspect, the methods of the present disclosure allow for the decoupling of Einlehner abrasion values and RDA/REA abrasion values. The techniques described herein can provide a dentifrice abrasion compound capable of providing improved pellicle cleaning ratio without damaging tooth tissues.

Dentifrice Composition

The inventive precipitated silica materials can be ready-to-use additives in the preparation of oral cleaning compositions, such as dentifrices, toothpastes, and the like. In one aspect, the heat treated precipitated silica material can be combined with one or more dentifrice components, such as, for example, abrasives, rheological aids, whiteners, sweeteners, flavoring additives, surfactants, colorants, or other components to form a dentifrice composition. If combined with other abrasives (such as any of the products offered by J. M. Huber Corporation under the trade name ZEODENT®), such an abrasive may be added in any amount. In one aspect, the inventive silica material can be used at a loading of about 20 wt. % in the dentifrice composition. In other aspects, the inventive silica material can be used in excess of 20% and up to about 25 wt. %, 30 wt. %, 35 wt. % or more.

The inventive silica material can be utilized alone as the cleaning agent component in a dentifrice compositions or in combination with one or more other abrasive materials. Thus, a combination of the inventive materials with other abrasives physically blended therewith within a suitable dentifrice formulation can be useful to accord targeted dental cleaning and abrasion results at a desired protective level. Thus, any number of other conventional types of abrasive additives may be present within inventive dentifrices in accordance with this invention. Other such abrasive particles include, for example, and without limitation, precipitated calcium carbonate (PCC), ground calcium carbonate (GCC), dicalcium phosphate or its dihydrate forms, silica gel (and of any structure), amorphous precipitated silica (by itself, and of any structure as well), perlite, titanium dioxide, calcium pyrophosphate, hydrated alumina, calcined alumina, insoluble sodium metaphosphate, insoluble potassium metaphosphate, insoluble magnesium carbonate, zirconium silicate, aluminum silicate, and so forth, can be introduced within the desired abrasive compositions to tailor the polishing characteristics of the target formulation (dentifrices, for example, etc.), if desired, as well.

In addition, as noted above, the inventive silica material can be used in conjunction with other abrasive materials, such as precipitated silica, silica gel, dicalcium phosphate, dicalcium phosphate dihydrate, calcium metasilicate, calcium pyrophosphate, alumina, calcined alumina, aluminum silicate, precipitated and ground calcium carbonate, chalk, bentonite, particulate thermosetting resins and other suitable abrasive materials known to a person of ordinary skill in the art.

In addition to the abrasive component, a dentifrice can optionally comprise one or more organoleptic enhancing agents. Organoleptic enhancing agents include humectants, sweeteners, surfactants, flavorants, colorants and thickening agents, (also sometimes known as binders, gums, or stabilizing agents). Humectants serve to add body or "mouth texture" to a dentifrice as well as prevent the dentifrice from drying out. Suitable humectants can comprise polyethylene glycol (at a variety of different molecular weights), propylene glycol, glycerin (glycerol), erythritol, xylitol, sorbitol, mannitol, lactitol, and hydrogenated starch hydrolyzates, as well as mixtures of these compounds. Typical levels of humectants, if present, can range from about 20 wt % to about 30 wt % of a dentifrice composition.

Sweeteners can be added to a dentifrice composition to impart a pleasing taste to the product. Suitable sweeteners include saccharin (as sodium, potassium or calcium saccharin), cyclamate (as a sodium, potassium or calcium salt), acesulfane-K, thaumatin, neohisperidin dihydrochalcone, ammoniated glycyrrhizin, dextrose, levulose, sucrose, mannose, and glucose.

In one aspect, surfactants can also be used in a dentifrice composition to make the composition more cosmetically acceptable. A surfactant, if used, can be a detersive material which imparts to the composition detersive and foaming properties. Surfactants are safe and effective amounts of anionic, cationic, nonionic, zwitterionic, amphoteric and betaine surfactants such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine and the like can be used in a dentifrice together with the inventive silica material. A surfactant, if present, is typically used in an amount of about 0.1 to about 15% by weight, preferably about 0.3% to about 5% by weight, such as from about 0.3% to about 2%, by weight.

Flavoring agents optionally can be added to dentifrice compositions. Suitable flavoring agents include, but are not limited to, oil of wintergreen, oil of peppermint, oil of spearmint, oil of sassafras, and oil of clove, cinnamon, anethole, menthol, thymol, eugenol, eucalyptol, lemon, orange and other such flavor compounds to add fruit notes, spice notes, etc. These flavoring agents can comprise mixtures of aldehydes, ketones, esters, phenols, acids, and aliphatic, aromatic and other alcohols.

In addition, colorants can be added to improve the aesthetic appearance of the dentifrice product. Suitable colorants are selected from colorants approved by appropriate regulatory bodies such as the FDA and those listed in the European Food and Pharmaceutical Directives and include pigments, such as $TiO_2$, and colors such as FD&C and D&C dyes.

Thickening agents can, in various aspect, be useful in the dentifrice compositions of the present invention to provide a gelatinous structure that stabilizes the toothpaste against phase separation. Suitable thickening agents include silica thickener; starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; as well as mixtures of these compounds. Typical levels of thickening agents or binders can range from about 0 wt % to about 15 wt % of a dentifrice composition.

Therapeutic agents are optionally used in the compositions of the present invention to provide for the prevention and treatment of dental caries, periodontal disease and temperature sensitivity. Examples of therapeutic agents, without intending to be limiting, are fluoride sources, such as sodium fluoride, sodium monofluorophosphate, potassium monofluorophosphate, stannous fluoride, potassium fluoride, sodium fluorosilicate, ammonium fluorosilicate and the like; condensed phosphates such as tetrasodium pyrophosphate, tetrapotassium pyrophosphate, disodium dihydrogen pyrophosphate, trisodium monohydrogen pyrophosphate; tripolyphosphates, hexametaphosphates, trimetaphosphates and pyrophosphates, such as; antimicrobial agents such as triclosan, bisguanides, such as alexidine, chlorhexidine and chlorhexidine gluconate; enzymes such as papain, bromelain, glucoamylase, amylase, dextranase, mutanase, lipases, pectinase, tannase, and proteases; quaternary ammonium compounds, such as benzalkonium chloride (BZK), benzethonium chloride (BZT), cetylpyridinium chloride (CPC), and domiphen bromide; metal salts, such as zinc citrate, zinc chloride, and stannous fluoride; sanguinaria extract and sanguinarine; volatile oils, such as eucalyptol, menthol, thymol, and methyl salicylate; amine fluorides; peroxides and the like. Therapeutic agents can be used in dentifrice formulations singly or in combination at a therapeutically safe and effective level.

In another aspect, preservatives can also be optionally added to the compositions of the present invention to prevent bacterial growth. Suitable preservatives approved for use in oral compositions such as methylparaben, propylparaben and sodium benzoate, or combinations thereof, may be added in safe and effective amounts.

The dentifrices disclosed herein can also a variety of additional ingredients such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like. Water can be used in a dentifrice composition to balance the composition, for example, from about 0 wt. % to about 60 wt. %, and provide desirable rheological properties.

In yet another aspect, silica thickeners for use within a dentifrice composition can include, as a non-limiting example, an amorphous precipitated silica such as ZEODENT® 165 silica. Other silica thickeners can comprise ZEODENT® 163 and/or 167 and ZEOFREE® 153, 177, and/or 265 silicas, all available from J. M. Huber Corporation, Havre de Grace Md., U.S.A.

The present invention can be described by any of the following exemplary and non-limiting aspects.

Aspect 1: A method for preparing a silica material, the method comprising heat treating a silica material comprising a metal compound, wherein the metal has a Mohs hardness value of at least about 5.5 in its oxide form, and wherein heat treating comprises heating the silica material at a temperature and for a period of time sufficient to dehydrate at least a portion of the metal compound disposed on a surface of the material.

Aspect 2: The method of Aspect 1, wherein heat treating comprises heating the silica material at a temperature of at least about 400° C. for at least about 8 hours.

Aspect 3: The method of Aspect 1, wherein heat treating comprises heating the silica material at a temperature of at least about 550° C. for at least about 8 hours.

Aspect 4: The method of Aspect 1, wherein, after heat treating, the silica material has a metal concentration of up to about 10 wt. %.

Aspect 5: The method of Aspect 1, wherein the silica material is prepared by contacting a silicate solution, an acidulating agent, and a soluble metal salt, wherein the soluble metal salt comprises a metal ion having a Mohs hardness value of at least 5.5 in its oxide form.

Aspect 6: The method of Aspect 5, wherein the metal ion comprises one or more of aluminum, tin, or a combination thereof.

Aspect 7: The method of Aspect 5, wherein the metal ion comprises aluminum.

Aspect 8: The method of Aspect 5, wherein the metal ion comprises tin.

Aspect 9: A silica material prepared by the method of Aspect 1.

Aspect 10: A dentifrice composition comprising the silica material of Aspect 9.

Aspect 11: A method for preparing a dentifrice material, the method comprising heat treating a silica material at a temperature of from about 400° C. to about 900° C. to form a heat treated silica material, and then contacting the heat treated silica material with one or more dentifrice components to form a dentifrice material.

Aspect 12: The method of Aspect 11, wherein heat treating comprises heating the silica material at a temperature of at least about 400° C. for at least about 8 hours.

Aspect 13: The method of Aspect 11, wherein heat treating comprises heating the silica material at a temperature of at least about 550° C. for at least about 8 hours.

Aspect 14: A dentifrice material prepared by the method of Aspect 11.

Aspect 15: A silica material having a loss on ignition at 900° C. of less than about 3 wt. %.

Aspect 16: A silica material having one or more of the following: a) a metal ion disposed on a surface thereof at a concentration of up to about 10 wt. %; b) a loss on ignition at 900° C. of less than about 3 wt. %; or c) an increased degree of polymerization as compared to a conventional silica material not exposed to a heat treatment step.

Aspect 17: The silica material of Aspect 16, having a metal ion disposed on a surface thereof at a concentration of up to about 4 wt. %.

Aspect 18: The silica material of Aspect 16, having an increased Einlehner abrasion value of at least about 150%, as compared to a conventional non heat treated precipitated silica.

Aspect 19: The silica material of Aspect 16, having an increase in RDA value of up to about 25% after heat treatment, as compared to a conventional non heat treated precipitated silica.

Aspect 20: A dentifrice composition comprising the silica material of any preceding Aspect.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Preparation of Silica Materials (Small Batch)

In a first example, metal doped silica materials were prepared using aluminum sulfate and stannous nitrate. The inventive silica materials were prepared on a two gallon scale, as described below.

Aluminum Sulfate 335 ml of sodium silicate solution (19.5%, 1.180 g/mL, 3.32 MR) and 835 ml of water were added to a 2 gallon reactor and heated to 87° C. while stirring at 300 RPM. Sodium silicate solution (19.5%, 1.180 g/mL, 3.32 MR) and sulfuric acid (17.1%, 1.12 g/mL, containing aluminum sulfate at a concentration of 0.15 mol alum/L acid solution) were then simultaneously added at 64 ml/min and 19.5 ml/min, respectively, for 47 minutes. After 47 minutes, the flow of silicate was stopped and the pH was adjusted to 5.5 with a continued flow of acid. Once pH 5.5 was reached, the batch was allowed to digest for 10 minutes at 90° C. After digestion, the batch was filtered and washed to a conductivity of about 1500 µS and was dried overnight at a temperature of 105° C. The batch was then mechanically milled, for example, with a hammer mill, to an average particle size of approximately 10 µm. The batch was then split into two parts. A first portion of the batch was used without heat treatment. The second portion of the batch was heated overnight at a temperature of 550° C.

Stannous Nitrate 335 ml of silicate (19.5%, 1.180 g/mL, 3.32 MR) and 835 ml of water were added to the 2 gallon reactor and heated to 87° C. with stirring at 300 RPM. Silicate (19.5%, 1.180 g/mL, 3.32 MR) and sulfuric acid (17.1%, 1.12 g/mL, containing stannous nitrate at a concentration of 0.29 mol stannous nitrate/L acid solution) were then simultaneously added at 64 ml/min and 19.5 ml/min, respectively, for 47 minutes. After 47 minutes, the flow of silicate was stopped and the pH was adjusted to 5.5 with continued flow of acid. Once pH 5.5 was reached, the batch was allowed to digest for 10 minutes at 90° C. After digestion, the batch was filtered and washed to a conductivity of about 1500 µS and was dried overnight at a temperature of 105° C. The batch was then hammer milled to an average particle size of approximately 10 µm. The batch was then split into two parts. A first portion of the batch was used without heat treatment. The second portion of the batch was heated overnight at a temperature of 550° C.

The resulting samples were examined to determine a variety of properties. Fluoride compatibility was determined by adding 7.0 g of silica abrasive (or 4.0 g of silica thickener) to a centrifuge tube containing 30.0 g of a 1624 ppm solution of F. After mixing, the solution was aged for 60 minutes on a rotating rack in an oven at 60° C. The samples were then centrifuged at 11,000 RPM for 15 minutes or until there were no silica particles remaining suspended in the solution. 10.0 ml of the centrifuged solution was then added to 10 ml of TISAB II buffer solution and the fluoride concentration was determined by fluoride ion selective electrode.

Metal content was determined by ion coupled plasma/optical emission spectroscopy (ICP/OES), wherein 2.0000 g of silica material was wet with a few drops of deionized water in a platinum crucible. 10 ml of perchloric acid (72%) and 10 ml of hydrofluoric acid (48-50%) were added and the platinum dish was slowly heated on a stir plate in a fume hood. As the platinum dish was heated, dense white fumes were evolved. The sides of the crucible were then carefully rinsed with boric acid (4%) and it was subsequently heated to fumes. After cooling, the contents of the crucible were transferred to a 250 ml volumetric flask and the crucible was washed with deionized water to make sure all remaining contents were quantitatively transferred. The dish was then rinsed with 5 ml of hydrochloric acid (36%) and the washings were added to the volumetric flask. Approximately 200 ml of deionized water were then added to the volumetric flask, and if the resulting solution was cloudy, it was heated on a low temperature hot plate until it became clear. After cooling, 2.50 ml of a scandium internal standard solution was added and the volumetric flask was filled to the mark with deionized water. The concentrations of the metals in the solution were then determined by ICP/OES.

TABLE 1

Summary of Physical Properties of Silica Materials Prepared using Aluminum and Tin

| | Aluminum | | Tin | |
|---|---|---|---|---|
| | Not Heated Aluminum Sulfate | Heat Treated | Not Heated Stannous Nitrate | Heat Treated |
| Moisture (%) | 3.6 | 1.6 | 4.7 | 0.8 |
| BET ($m^2/g$) | 232 | 44 | 30 | 23 |
| CTAB ($m^2/g$) | 44 | 40 | 84 | 45 |
| Median particle size (μm) | 8.0 | 9.3 | 3.5 | 4.9 |
| Sodium sulfate (%) | <0.35 | <0.35 | <0.35 | <0.35 |
| Oil absorption (cc/100 g) | 54 | 50 | 46 | 48 |
| 5% Ph | 8.2 | 8.4 | 9.0 | 8.1 |
| Al (%) | 1.28 | 1.39 | 0.07 | 0.06 |
| Zn (%) | — | — | — | — |
| Sn (%) | — | — | 5.7 | 5.5 |
| Ca (ppm) | — | — | 518 | 405 |
| Fe (ppm) | 188 | 217 | 206 | 229 |
| Mg (ppm) | 48 | 49 | 32 | 44 |
| $Na_2O$ (%) | 2.1 | 2.2 | 1.8 | 1.7 |
| Fluoride compatibility (%) | 34 | 52 | 77 | 97 |
| Einlehner (mg lost/100k rev) | 7.4 | 18.0 | 18.0 | 34.8 |

The chemical and physical properties from analysis of each of the precipitates silica materials are illustrated in Table 1. The silicas produced were low structure, with oil absorption values ranging from 50-61 cc/100 g. The oil absorption and the CTAB values did not substantially change upon heating to 550° C., indicating that the meso and macro porosity were not dramatically impacted by the heating step. Although the BET surface area was reduced in both cases, the reduction was likely due to a collapse in volume in the micro porosity range. The Einlehner values for all samples increased upon heating. While not wishing to be bound by theory, this increase was likely due to further polymerization of the Si—O—Si groups in the silica particles and the dehydration of the metal adduct on the silica, resulting in the formation of a less hydrated metal oxide species. Since the heat treatment of the silica particles resulted in an increase in wall density and an increase in the Mohs hardness of the metal oxide species (ex. 9.0 for alpha-alumina and ~6.5 for stannous oxide), the resulting Einlehner values were increased. Fluoride availability values for the metal containing silica, with the exception of the aluminum containing sample, were not negatively impacted with the introduction of the metal species into the silica.

Example 2

Preparation of Silica Materials (Large Batch)

In a second example, silica materials were prepared in 30 gallon batches, as described below.

Silica (No Metal Adduct)

5.6 L of silicate (19.5%, 1.180 g/mL, 3.32 MR) and 13.9 L of water were added to the 30 gallon reactor and heated to 87° C. while stirring at 150 RPM. Silicate (19.5%, 1.180 g/mL, 3.32 MR) and sulfuric acid (17.1%, 1.12 g/mL) were then simultaneously added at 1.1 L/min and 0.33 L/min, respectively, for 47 minutes. After 47 minutes, the flow of silicate was stopped and the pH was adjusted to 5.5 with continued flow of acid. Once pH 5.5 was reached, the batch was allowed to digest for 10 minutes at 90° C. After digestion, the batch was filtered and washed to a conductivity of about 1500 μS and was spray dried. The batch was hammer milled to an average particle size of approximately 10 μm. The silica was then split into two parts. One portion of the batch was utilized without further heat treatment. The second portion of the batch was heated overnight at a temperature of 550° C.

Aluminum 5.6 L of silicate (19.5%, 1.180 g/mL, 3.32 MR) and 13.9 L of water were added to the 30 gallon reactor and heated to 87° C. while stirring at 150 RPM. Silicate (19.5%, 1.180 g/mL, 3.32 MR) and sulfuric acid (17.1%, 1.12 g/mL, containing 0.25 mol alum/L of acid solution) were then simultaneously added at 1.1 L/min and 0.33 L/min, respectively, for 47 minutes. After 47 minutes, the flow of silicate was stopped and the pH was adjusted to 5.5 with continued flow of acid. Once pH 5.5 was reached, the batch was allowed to digest for 10 minutes at 90° C. After digestion, the batch was filtered and washed to a conductivity of ~1500 μS and was spray dried. The batch was hammer milled to an average particle size of approximately 10 μm. The silica was then split into two parts. One portion of the batch was utilized without further heat treatment. The second portion of the batch was heated overnight at a temperature of 550° C.

Silica (No Metal Adduct)

1.9 L of silicate (19.5%, 1.180 g/mL, 3.32 MR) and 4.8 L of water were added to the 30 gallon reactor and heated to 87° C. while stirring at 150 RPM. Silicate (19.5%, 1.180 g/mL, 3.32 MR) and sulfuric acid (17.1%, 1.12 g/mL) were then simultaneously added at 1.1 L/min and 0.35 L/min, respectively, for 47 minutes. After 47 minutes, the flow of silicate was stopped and the pH was adjusted to 5.5 with continued flow of acid. Once pH 5.5 was reached, the batch was allowed to digest for 10 minutes at 90° C. After digestion, the batch was filtered and washed to a conductivity of about 1500 μS and was spray dried. The batch was hammer milled to an average particle size of approximately 10 μm. The silica was then split into two parts. One portion of the batch was utilized without further heat treatment. The second portion of the batch was heated overnight at a temperature of 550° C.

Aluminum 1.9 L of silicate (19.5%, 1.180 g/mL, 3.32 MR) and 4.8 L of water were added to the 30 gallon reactor and heated to 87° C. while stirring at 150 RPM. Silicate (19.5%, 1.180 g/mL, 3.32 MR) and sulfuric acid (17.1%, 1.12 g/mL, containing 0.25 mol alum/L of acid solution) were then simultaneously added at 1.1 L/min and 0.35 L/min, respectively, for 47 minutes. After 47 minutes, the flow of silicate was stopped and the pH was adjusted to 5.5 with continued flow of acid. Once pH 5.5 was reached, the batch was allowed to digest for 10 minutes at 90° C. After digestion, the batch was filtered and washed to a conductivity of about 1500 μS and was spray dried. The batch was hammer milled to an average particle size of approximately 10 μm. The silica was then split into two parts. One portion of the batch was utilized without further heat treatment. The second portion of the batch was heated overnight at a temperature of 550° C.

Zeolex 7A

A control sample of Zeolex® 7A silica was split into equal portions. One portion was utilized without further heat treatment. The second portion was heated overnight at a temperature of 550° C.

The physical properties of the silicas prepared in the 30-gallon reactor are shown in Table 2. Silica samples and their corresponding analogues containing ~3% Al were prepared at structure levels ranges of ~60-80 and 45-60 cc/100 g. Heat treatment overnight at 550° C. resulted in a slight decrease in oil absorption and water absorption values for all samples tested. The BET surfaced area values dropped considerably after heating, likely due to the collapse of microporosity in the samples. The Einlehner values also increased for all samples tested, both with and without aluminum present.

TABLE 2

Summary of physical properties from 30-gallon batches

| | Silica (no metal) | | Aluminum | | Silica (no metal) | | Aluminum | | Zeolex 7A | |
|---|---|---|---|---|---|---|---|---|---|---|
| | Not Heated | Heated | Not Heated | Heated | Not Heated | Heated | Not Heated | Heated | Not Heated | Heated |
| Moisture (%) | 5.9 | 0.7 | 7.4 | 0.1 | 4.9 | 0.2 | 4.1 | 0.8 | | 0.6 |
| BET ($m^2/g$) | 118 | 40 | 311 | 98 | 63 | 29 | 282 | 69 | | 119 |
| CTAB ($m^2/g$) | 32 | 29 | 77 | 59 | 26 | 24 | 49 | 39 | | 125 |
| Median particle size (μm) | 9.3 | 9.5 | 8.3 | 8.0 | 10.0 | 10.9 | 7.5 | 8.0 | | 9.5 |
| Sodium sulfate (%) | 1.38 | 1.91 | 1.95 | 2.13 | 0.89 | 1.42 | 1.38 | 1.64 | | |
| Oil absorption (cc/100 g) | 79 | 71 | 72 | 63 | 63 | 53 | 50 | 47 | | 120 |
| Water AbC (cc/100 g) | 104 | 93 | 98 | 89 | 82 | 69 | 73 | 67 | | 166 |
| 5% pH | 7.8 | 7.2 | 7.7 | 8.6 | 8.8 | 8.3 | 7.9 | 8.7 | | 7.3 |
| LOI (%) | 5.4 | 1.9 | 7.5 | 2.8 | 6.1 | 1.8 | 9.4 | 2.1 | | |
| Al (%) | 0.07 | 0.07 | 2.80 | 3.36 | 0.12 | 0.14 | 2.85 | 3.39 | | 5.0 |
| Zn (%) | — | — | — | — | — | — | — | — | | — |
| Sn (%) | — | — | — | — | — | — | — | — | | — |
| Ca (ppm) | 268 | 343 | 125 | 129 | 714 | 786 | 220 | 272 | | — |
| Fe (ppm) | 218 | 198 | 145 | 173 | 178 | 189 | 142 | 161 | | — |
| Mg (ppm) | 82 | 96 | 72 | 87 | 343 | 366 | 122 | 145 | | — |
| $Na_2O$ (%) | 0.92 | 1.04 | 2.40 | 2.88 | 1.01 | 1.17 | 2.32 | 2.69 | | — |
| Powder XRD | | | | | Amorphous | | | | | |
| Fluoride compatibility (%) | 96 | 99 | 30 | 39 | 89 | 99 | 33 | 43 | | |
| Einlehner (mg lost/100k rev) | 6.5 | 16.3 | 3.2 | 18.1 | 14.9 | 36.5 | 5.9 | 18.6 | | |

Silica and Aluminum samples were formulated into toothpaste compositions at 20% loading, as described in Table 3, below. PCR and RDA testing were performed on the resulting toothpaste compositions.

TABLE 3

Toothpaste formulation used for PCR/RDA testing.

| | Example # | | | | | | |
|---|---|---|---|---|---|---|---|
| | T1 | T2 | T3 | T4 | T5 | T6 | T7 |
| Glycerin (99.7%) | 11.00 | 11.00 | 11.00 | 11.00 | 11.00 | 11.00 | 11.00 |
| Sorbitol (70%) | 40.00 | 40.00 | 40.00 | 40.00 | 40.00 | 40.00 | 40.00 |
| Deionized Water | Q.S. | Q.S. | Q.S. | Q.S. | Q.S. | Q.S. | Q.S. |
| PEG-12 | 3.00 | 3.00 | 3.00 | 3.00 | 3.00 | 3.00 | 3.00 |
| Cekol 2000 | 1.20 | 1.20 | 1.20 | 1.20 | 1.20 | 1.20 | 1.20 |
| Tetrasodium pyrophosphate | 0.50 | 0.50 | 0.50 | 0.50 | 0.50 | 0.50 | 0.50 |
| Sodium saccharin | 0.20 | 0.20 | 0.20 | 0.20 | 0.20 | 0.20 | 0.20 |
| Sodium fluoride | 0.24 | 0.24 | 0.24 | 0.24 | 0.24 | 0.24 | 0.24 |
| Thickening Silica | | | | | | | |
| Zeodent 165 Abrasive Silica | 1.50 | | | | | | |
| Silica (no metal) - Not Heat Treated | 20.00 | — | — | — | — | — | — |

TABLE 3-continued

Toothpaste formulation used for PCR/RDA testing.

| | Example # | | | | | | |
|---|---|---|---|---|---|---|---|
| | T1 | T2 | T3 | T4 | T5 | T6 | T7 |
| Silica (no metal) - Heat Treated | — | 20.00 | — | — | — | — | — |
| Aluminum - Not Heat Treated | — | — | 20.00 | — | — | — | — |
| Aluminum - Heat Treated | — | — | — | 20.00 | — | — | — |
| Zeodent 103 | — | — | — | — | 20.00 | — | — |
| Zeolex 7A - Not Heat Treated | — | — | — | — | — | 20.00 | — |
| Zeolex 7A - Heat Treated | — | — | — | — | — | — | 20.00 |
| Titanium dioxide | 0.50 | 0.50 | 0.50 | 0.50 | 0.50 | 0.50 | 0.50 |
| Sodium lauryl sulfate | 1.20 | 1.20 | 1.20 | 1.20 | 1.20 | 1.20 | 1.20 |
| Flavor | 0.65 | 0.65 | 0.65 | 0.65 | 0.65 | 0.65 | 0.65 |
| Total | 100 | 100 | 100 | 100 | 100 | 100 | 100 |

TABLE 4

Summary of PCR/RDA results.

| | Example # | | | | | | |
|---|---|---|---|---|---|---|---|
| | T1 | T2 | T3 | T4 | T5 | T6 | T7 |
| PCR #1 (IU, 20% loading) | 83 | 95 | 79 | 98 | 82 | 38 | 61 |
| PCR #2 (IU, 20% loading) | 101 | 109 | 94 | 104 | 103 | 56 | 79 |
| Average PCR | 92 | 102 | 87 | 101 | 93 | 47 | 70 |
| PCR Increase (%) | | 11 | | 16 | — | | 49 |
| RDA (IU, 20% loading) | 190 | 207 | 177 | 217 | 184 | 28 | 54 |

PCR testing indicated that both silica (without a metal adduct) and silica samples containing aluminum achieved higher values after heat treatment. The average PCR increase for the silica sample was 11% and the average increases for silica samples containing aluminum increased by 16 and 49%. The RDA increased in each case, but the RDA values were still in the normal range typically observed for precipitated silica abrasives.

What is claimed is:

1. A method for preparing a heat treated silica material, the method comprising heat treating a precipitated silica material comprising a metal, wherein the metal has a Mohs hardness value of at least about 5.5 in its oxide form, and wherein heat treating comprises heating the precipitated silica material at a temperature and for a period of time sufficient to produce the heat treated silica material, which is characterized by a loss on ignition at 900° C. of less than about 3 wt. %, and wherein:
   an Einlehner abrasion value of the heat treated silica material is from about 90% to about 450% greater than an Einlehner abrasion value of the precipitated silica material.

2. The method of claim 1, wherein heat treating comprises heating the precipitated silica material at a temperature of at least about 400° C. for at least about 8 hours.

3. The method of claim 1, wherein heat treating comprises heating the precipitated silica material at a temperature of at least about 550° C. for at least about 8 hours.

4. The method of claim 1, wherein the heat treated silica material has a metal concentration of from about 1 wt. % up to about 10 wt. %.

5. The method of claim 1, wherein the precipitated silica material is prepared by contacting a silicate solution, an acidulating agent, and a soluble metal salt, wherein the soluble metal salt comprises a metal ion having a Mohs hardness value of at least 5.5 in its oxide form.

6. The method of claim 5, wherein the metal ion comprises one or more of aluminum, tin, or a combination thereof.

7. The method of claim 5, wherein the metal ion comprises aluminum.

8. The method of claim 5, wherein the metal ion comprises tin.

9. A heat treated silica material prepared by the method of claim 1.

10. A dentifrice composition comprising the heat treated silica material of claim 9.

11. A method for preparing a dentifrice material, the method comprising heat treating a precipitated silica material comprising aluminum and/or tin at a temperature of from about 400° C. to about 900° C. to form a heat treated silica material, and then contacting the heat treated silica material with one or more dentifrice components to form the dentifrice material; wherein:
   the heat treated silica material has a loss on ignition at 900° C. of less than about 3 wt. %, which wherein
   an Einlehner abrasion value of the heat treated silica material is from about 90% to about 450% greater than an Einlehner abrasion value of the precipitated silica material.

12. The method of claim 11, wherein heat treating comprises heating the precipitated silica material at a temperature of from about 400° C. to about 900° C. for at least about 8 hours.

13. The method of claim 11, wherein heat treating comprises heating the precipitated silica material at a temperature of from about 550° C. to about 900° C. for at least about 8 hours.

14. A dentifrice material prepared by the method of claim 11.

15. The method of claim 1, wherein the precipitated silica material comprises silica particles.

16. The method of claim 1, wherein the precipitated silica material comprises aluminosilicate particles.

17. The method of claim 1, wherein the metal comprises aluminum, tin, or a combination thereof.

18. The method of claim 5, wherein the metal salt comprises a sulfate, a nitrate, a phosphate, or a carbonate of aluminum or tin.

19. A precipitated silica material comprising from about 1 wt. % to about 10 wt. % of a metal having a Mohs hardness value of at least 5.5 in its oxide form, and wherein the precipitated silica material is characterized by:

a loss on ignition at 900° C. of less than about 3 wt. %; and a pellicle cleaning ratio (PCR) at 20% loading of at least 90.

20. The silica material of claim 19, wherein the metal comprises aluminum.

21. The silica material of claim 19, wherein the metal comprises tin.

22. The silica material of claim 19, wherein the precipitated silica material comprises aluminosilicate particles.

23. The silica material of claim 19, wherein the precipitated silica material is further characterized by an Einlehner abrasion value in a range from 18 to 34.8 mg lost/100,000 revolutions.

24. A dentifrice composition comprising the silica material of claim 19.

* * * * *